United States Patent
Fenton et al.

(10) Patent No.: US 6,893,434 B2
(45) Date of Patent: May 17, 2005

(54) ULTRASONIC SOFT TISSUE CUTTING AND COAGULATION SYSTEMS INCLUDING A RETRACTABLE GRASPER

(75) Inventors: Paul Fenton, Marblehead, MA (US); Francis Harrington, Peabody, MA (US); Paul Westhaver, Newburyport, MA (US)

(73) Assignee: Axya Medical, Inc., Beverly, MA (US)

( * ) Notice: Subject to any disclaimer, the term of this patent is extended or adjusted under 35 U.S.C. 154(b) by 97 days.

(21) Appl. No.: 10/436,823

(22) Filed: May 13, 2003

(65) Prior Publication Data

US 2003/0212391 A1 Nov. 13, 2003

Related U.S. Application Data

(60) Provisional application No. 60/380,176, filed on May 13, 2002.

(51) Int. Cl.$^7$ ............................................. A61B 18/18
(52) U.S. Cl. .................. 606/37; 606/169; 606/170; 606/171; 606/27; 606/41; 607/96; 607/98; 604/22
(58) Field of Search .................. 606/27, 37, 39–40, 606/45, 169; 604/22; 607/96, 98, 99

(56) References Cited

U.S. PATENT DOCUMENTS

| | | | |
|---|---|---|---|
| 5,322,055 A | | 6/1994 | Davison et al. |
| 5,906,628 A | * | 5/1999 | Miyawaki et al. .......... 606/169 |
| 6,036,667 A | | 3/2000 | Manna et al. |
| 6,056,735 A | | 5/2000 | Okada et al. |
| 6,193,709 B1 | * | 2/2001 | Miyawaki et al. ............. 606/1 |

* cited by examiner

*Primary Examiner*—Beverly M. Flanagan
*Assistant Examiner*—Matthew Kasztejna
(74) *Attorney, Agent, or Firm*—McDermott Will & Emery LLP

(57) ABSTRACT

The present invention features an ultrasonic surgical system including an ultrasonically vibrating blade, and retractable grasper. The grasper includes a grasping jaw or clamp that is movable, in a direction perpendicular to the primary vibratory mode of the ultrasonic blade element, from an open, extended position to a closed position in which tissue is grasped between the jaw and the vibrating blade, and to a retracted position for storage. The jaw is preferably hinge-actuated.

8 Claims, 2 Drawing Sheets retracted position

Extended position

Jaw closes against blade to grasp tissue closed position

ULTRASONIC SOFT TISSUE CUTTING AND COAGULATION SYSTEMS INCLUDING A RETRACTABLE GRASPER

CROSS-REFERENCE TO RELATED APPLICATIONS

The present application claims priority to provisional U.S. patent application Ser. No. 60/380,176, filed on May 13, 2002, which is assigned to the assignee of the present application and incorporated herein by reference.

STATEMENT REGARDING FEDERALLY SPONSORED RESEARCH

Not Applicable

REFERENCE TO MICROFICHE APPENDIX

Not Applicable

BACKGROUND OF THE INVENTION

For many years, ultrasonic surgical instruments have been used for soft tissue cutting and coagulation. These ultrasonic instruments include ultrasonic transducers which convert the electric energy supplied by a generator into ultrasonic frequency vibratory energy, which can then be applied to the tissue of a patient. Ultrasonic surgical instruments use relatively high-power, low-frequency vibratory energy, typically at a frequency range of about 20 kHz to about 100 kHz.

In general, ultrasonic soft tissue cutting and coagulation systems include a member that is coupled to the ultrasonic transducers, and that can be made to vibrate at ultrasonic frequencies. The ultrasonically vibrating probe is then applied to the tissue, in order to transmit ultrasonic energy to the tissue. In this way, the contacted tissue can be cut or coagulated. Ultrasonic surgical systems offer a number of advantages over conventional surgical systems, for example reduction of bleeding and trauma.

The mechanism through which the ultrasonic probe and the tissue interact, i.e. the physics of ultrasonic soft tissue cutting and coagulation, is not completely understood, however various explanations have been provided by researchers over the years. These explanations include descriptions of mechanical effects and thermal effects. The mechanical viewpoint states that the vibrating tip of the ultrasonic probe generates short-range forces and pressures, which are sufficient to dislodge cells in the tissue, and break up the tissue structures. Various types of forces are postulated as contributing to the rupture of the tissue layer, for example the impact forces resulting from the direct contact of the vibrating tip with tissue, and the shear forces that are the result of the differences in force levels across tissue boundaries. Some energy may be lost due to frictional heating, and by the heating caused by the absorption of acoustic energy by tissue.

Thermal effects may include frictional heat, generated by the ultrasonically vibrating tip, in an amount sufficient to melt a portion of the contacted tissue. Alternatively, the tissue may absorb the vibratory energy, which it then converts into heat. The generated heat may be used to coagulate a blood vessel, by way of example. Other effects that have been postulated in order to explain the probe-tissue interaction include cavitational effects. The cavitation viewpoint postulates that the coupling of ultrasonic energy onto tissue results in the occurrence of cavitation in tissue, namely the formation of gas or vapor-filled cavities or bubbles within the tissue, which may oscillate and propagate. A combination of mechanical, thermal, and cavitational effects may result in the desired surgical outcomes, such as cutting and coagulation.

A number of ultrasonic soft tissue cutting and coagulating systems have been disclosed in the prior art. For example, U.S. Pat. No. 5,322,055 (the "'055 patent"), assigned on its face to Ultracision, Inc., discloses ultrasonic surgical instruments having a non-vibrating clamp for pressing tissue against an ultrasonically vibrating blade, for cutting, coagulating, and blunt-dissecting of tissue. When ultrasonically activated, the blade undergoes longitudinal mode vibrations, parallel to the blade edge. U.S. Pat. No. 6,036,667 (the "'667 patent"), assigned on its face to United States Surgical Corporation and to Misonix Incorporated, discloses an ultrasonic dissection and coagulation system. The ultrasonic system includes an ultrasonic cutting blade, and a clamp member for clamping tissue in conjunction with the blade. The blade has a cutting surface that is angled with respect to the longitudinal axis of the elongated body portion of the system.

U.S. Pat. No. 6,056,735 (the "'735 patent"), assigned on its face to Olympus Optical Co., Ltd., relates to ultrasonic treatment systems, including endoscopic systems and aspiration systems, for treating living tissue. The '735 patent features an ultrasonic treatment system including a probe which conveys ultrasonic vibrations to a stationary distal member. The stationary distal member cooperate with a movable holding member to clamp or free tissue, when manipulated by a scissors-like manipulating means.

In the prior art patents discussed above, the ultrasonically vibrating member must cooperate with a clamp or jaw, in order to grasp the tissue that is being treated. It is desirable to provide systems having a blade/jaw assembly, in which the ultrasonically vibrating member can operate (in conjunction with the jaw) without having to perform, by itself, a grasping function.

SUMMARY OF THE INVENTION

The present invention features an ultrasonic surgical system including a retractable grasper. The grasper includes a grasping jaw or clamp that is movable in a direction perpendicular to the primary vibratory mode of the ultrasonic blade element. The jaw is preferably hinge-actuated, and is operable to grasp tissue. The jaw is movable between an open, extended position, to a closed position in which the jaw presses against the blade element, in a direction substantially parallel to the direction of vibration of the blade. In this way, tissue is grasped between the jaw and the blade. The grasper allows the ultrasonic blade to be used without need for the blade itself to perform a grasping function.

BRIEF DESCRIPTION OF THE DRAWINGS

The invention can be more fully understood by referring to the following detailed description taken in conjunction with the accompanying drawings, in which.

DETAILED DESCRIPTION

The present invention is directed to an ultrasonic surgical system having a retractable grasper that allows an ultrasonically vibrating member to operate in conjunction with a jaw, without requiring the vibrating member itself to perform a grasping function.

Figure 1:
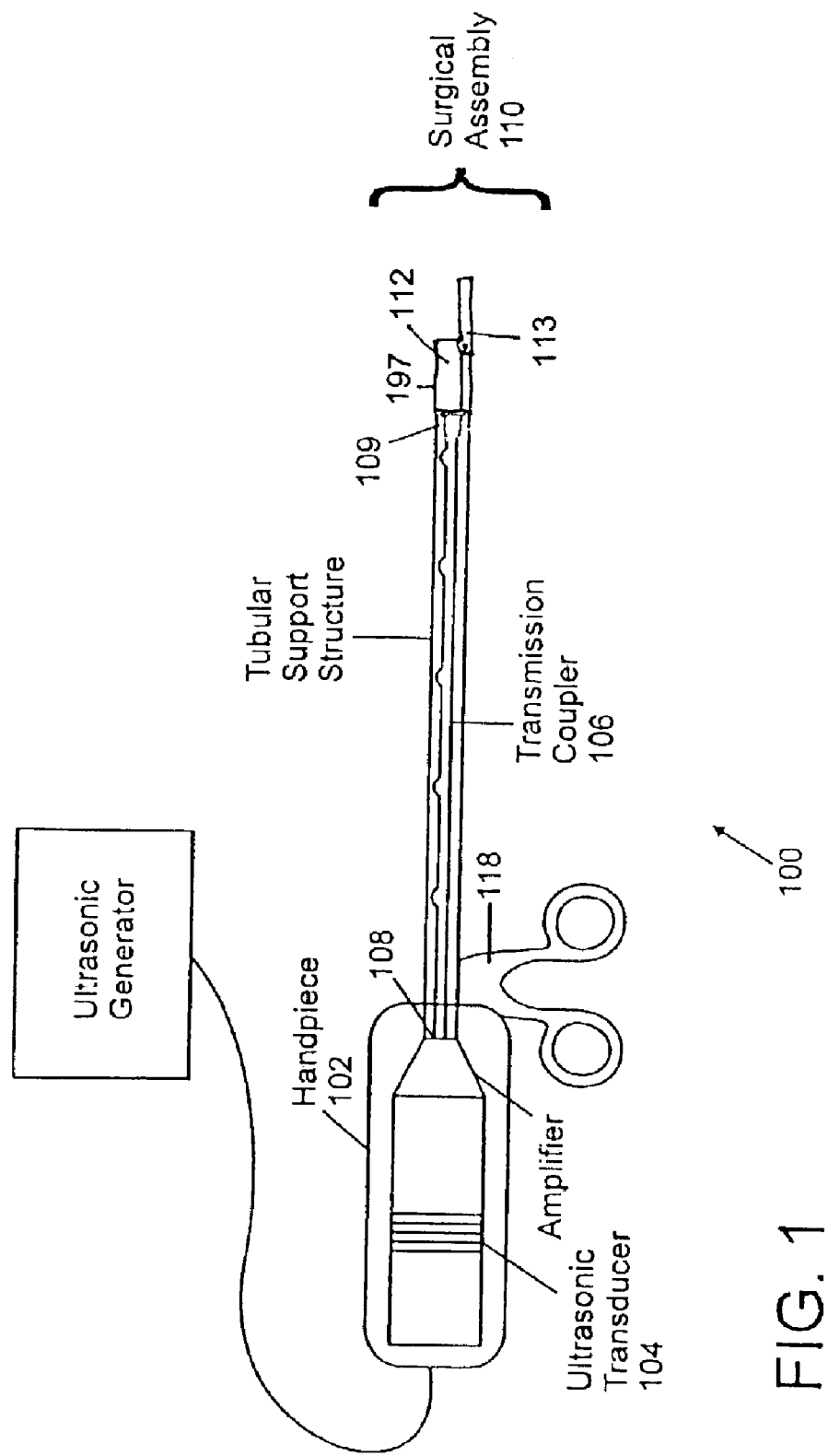
FIG. 1 illustrates an overall schematic view of an ultrasonic surgical system, constructed in accordance with the present invention.

FIG. 1 illustrates an overall schematic view of an ultrasonic soft tissue cutting and coagulating system 100, constructed in accordance with one embodiment of the present invention. The system include a handpiece 102 that encloses one or more ultrasonic transducers 104. An ultrasonic generator is connected to the handpiece 102, and supplies electric energy. The transducers 104 convert the supplied electric energy into ultrasonic frequency vibratory energy. The frequency range at which the system 100 operates is typically between about 20 kHz and about 100 kHz, and the electric power supplied by the ultrasonic generator is typically between about 100 W to about 150 W, although other frequencies and power levels can be used. The ultrasonic transducers 104 may be made of piezoelectric material, or may be made of other materials, such as nickel, that are capable of converting electric energy into vibratory energy. The handpiece 102 may also enclose an amplifier, for example an acoustic horn, which amplifies the mechanical vibrations generated by the ultrasonic transducers 104.

An elongated ultrasonic transmission coupler 106 is connected to the handpiece 102. In one embodiment, the transmission coupler 106 has a proximal end 108 and a distal end 109, and is connected to the handpiece 102 at the proximal end. The ultrasonic transmission coupler 106 transmits the ultrasonic vibratory energy, received from the transducers 104, from its proximal 108 end to its distal end 109. In one embodiment, a sheath 190 may enclose the transmission coupler 106.

In the illustrated embodiment, an ultrasonic surgical assembly 110 is connected to the distal end 109 of the elongated transmission coupler 106, and includes an ultrasonic blade element 112, and a retractable grasper 113. Preferably, the blade element 112 includes an elongated blade edge 197. The blade element 112 is acoustically coupled to the transmission coupler 106, so that the ultrasonic energy is transmitted to, and carried by, the blade element 112.

The blade element 112 undergoes vibratory motion upon receipt of ultrasonic vibrations from the transducer(s) 104. The blade element 112 thereby delivers ultrasonic energy to the contacting tissue, so that desired surgical effects, such as cutting and/or coagulation, can be achieved. In one form of the invention, the blade element undergoes ultrasonic vibrations characterized by at least one primary vibratory mode. In one embodiment, the primary vibratory mode may be along a longitudinal direction substantially parallel to the blade edge. The retractable grasper 113 includes a grasping jaw 114, which is operable to close against the blade element 112, so as to engage tissue between their respective operative surfaces.

In one embodiment, the present invention is directed to an accessory for an ultrasonic surgical instrument having an ultrasonic transducer for generating ultrasonic vibrations, and an elongated ultrasonic transmission coupler connected to the transducer to receive ultrasonic vibrations therefrom. The accessory includes a clamp assembly connected to the transducer. The clamp assembly includes a blade element, and a retractable clamp jaw movable relative to the blade element. The clamp jaw is movable from an extended position to a closed position in which the blade element and the clamp jaw are in engagement so as to capture tissue therebetween. The clamp jaw is further movable to a retracted position, suitable for storing the accessory.

Figure 2A:
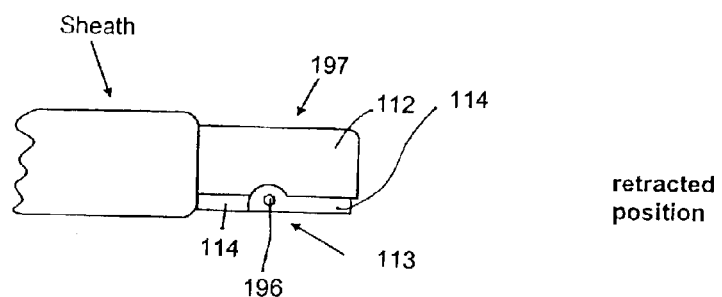
FIG. 2A illustrates a grasper, constructed according to one embodiment of the present invention, and shown in a retracted state.
Figure 2B:
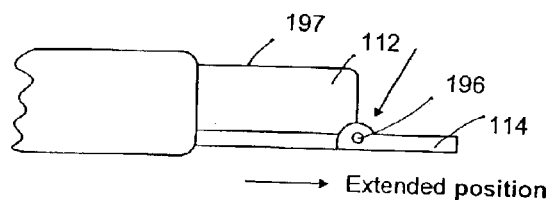
FIG. 2B illustrates an extended state of the grasper.
Figure 2C:
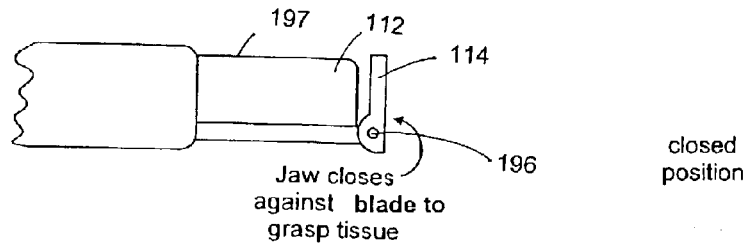
FIG. 2C illustrates the hinge-actuated jaw that closes against the ultrasonic blade, so as to grasp tissue.

FIGS. 2A–2C illustrate a grasper 113, constructed according to one embodiment of the present invention. The grasper 113 is retractable and extendable, i.e. the grasping jaw 114 is movable from an extended position to a closed position in which the blade element and the jaw are in engagement so as to capture tissue therebetween, and is further movable to a retracted position.

The retracted position is shown in FIG. 2A. When the ultrasonic system 100 is not in use, the grasper 113 can be stored in the retracted position. The grasper 113 in an extended state is illustrated in FIG. 2B. In this configuration, the grasping jaw 114 lies along a horizontal direction substantially parallel to the primary longitudinal mode of vibration of the ultrasonic blade element.

Preferably, a jaw activating mechanism is provided for moving the jaw relative to the blade element, from the extended position to the closed position, and again to the retracted position. In one embodiment, the jaw activating mechanism is a hinge. In this embodiment, the grasping jaw is hinge-actuated, i.e. is pivotable about a pivot point 196 from an open position to a closed position in which the jaw closes against the ultrasonic blade so as to grasp tissue therebetween, and subsequently to a retracted position, for storage. In the extended state, the pivot point 196 is preferably aligned with the elongated edge 197 of the ultrasonic blade, and the grasping jaw 114 extends beyond the elongated edge, along the horizontal direction.

The jaw 114 is operable to move, in a direction substantially perpendicular to the primary vibratory mode of the ultrasonic blade, from the open, extended position described above to a closed position illustrated in FIG. 2C. FIG. 2C illustrates the hinge-actuated jaw that closes against the ultrasonic blade, so as to grasp tissue. As seen in FIG. 2C, the jaw closes against the blade in a direction substantially parallel to the direction of the ultrasonic vibrations. The tissue being treated is thereby grasped, between the jaw and the blade. In this way, tissue can be grasped, without requiring the ultrasonic blade by itself to perform a grasping function.

What is claimed is:

1. An ultrasonic surgical instrument, comprising:
    a. an ultrasonic transducer for generating ultrasonic vibrations;
    b. a grasper assembly connected to said transducer, said grasper assembly including:
        i) a blade element extending along a central axis to a distal tip; and
        ii) a pivotable, elongated grasping jaw movable relative to said blade element in the direction of said axis, said jaw being movable from an extended position, wherein said elongated jaw extends along said axis and beyond said distal tip, to a closed position, in which said jaw extends transverse to said axis and opposite to said distal tip and the distal tip of said blade element and the jaw are adapted to capture tissue therebetween, said jaw being further movable to a retracted position in which said jaw extends along said axis and extends no further than said distal tip of said blade element.

2. An ultrasonic surgical instrument according to claim 1, wherein said blade element has an elongated blade edge.

3. An ultrasonic surgical instrument according to claim 1, wherein said blade is coupled to said transducer for receiving ultrasonic vibrations therefrom so as to undergo ultrasonic vibrations characterized by at least one primary vibratory mode.

4. An ultrasonic surgical instrument according to claim 2,
   wherein said blade element is coupled to said transducer for receiving ultrasonic vibrations therefrom so as to undergo ultrasonic vibrations characterized by at least one primary vibratory mode; and
   wherein said primary vibratory mode is along a longitudinal direction substantially parallel to said blade edge.

5. An ultrasonic surgical instrument according to claim 4, wherein said jaw is movable relative to said blade element in a direction substantially perpendicular to said primary vibratory mode.

6. An ultrasonic surgical instrument according to claim 1, further comprising a jaw activating mechanism for moving said jaw relative to said blade element from said extended position to said closed position, and from said extended position to said retracted position.

7. An ultrasonic surgical instrument according to claim 6, wherein said jaw activating mechanism comprises a hinge that actuates the motion of the jaw from said extended position to said closed position, and from said extended position to said retracted position.

8. An accessory for an ultrasonic surgical instrument having an ultrasonic transducer for generating ultrasonic vibrations, and an elongated ultrasonic transmission coupler connected to said transducer and adapted to receive ultrasonic vibrations therefrom and transmit said vibrations from one end of said coupler to the other end, said accessory comprising:
   a. a clamp assembly connected to said transducer, said clamp assembly including:
      i) a blade element; and
      ii) a retractable clamp jaw movable relative to said blade element, said clamp jaw being movable front an extended position to a closed position in which said clamp jaw opposes an end of said blade element wherein the end of the blade element and the clamp jaw are adapted to capture tissue therebetween, said clamp jaw being further movable to a retracted position, in which said jaw extends no further than the end of said blade element.

* * * * *

UNITED STATES PATENT AND TRADEMARK OFFICE
CERTIFICATE OF CORRECTION

PATENT NO. : 6,893,434 B2
DATED : May 17, 2005
INVENTOR(S) : Melvin Levinson

It is certified that error appears in the above-identified patent and that said Letters Patent is hereby corrected as shown below:

Column 6,
Line 12, after "movable" and before "an", delete "front", and insert thereof -- from --.

Signed and Sealed this

Twelfth Day of July, 2005

JON W. DUDAS
*Director of the United States Patent and Trademark Office*